(12) United States Patent
Fukuhara et al.

(10) Patent No.: US 7,896,932 B2
(45) Date of Patent: Mar. 1, 2011

(54) NON-OXIDATIVE HAIR DYE COMPOSITION

(75) Inventors: Masaki Fukuhara, Tokyo (JP); Masakazu Yamaguchi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/682,618

(22) PCT Filed: Oct. 10, 2008

(86) PCT No.: PCT/JP2008/002882

§ 371 (c)(1),
(2), (4) Date: Apr. 12, 2010

(87) PCT Pub. No.: WO2009/047914

PCT Pub. Date: Apr. 16, 2009

(65) Prior Publication Data

US 2010/0218320 A1    Sep. 2, 2010

(30) Foreign Application Priority Data

Oct. 12, 2007  (JP) .............................. 2007-267058

(51) Int. Cl.
*A61Q 5/10* (2006.01)
(52) U.S. Cl. ................. 8/405; 8/453; 8/455; 8/465; 8/589; 8/676
(58) Field of Classification Search ........ 8/405, 8/453, 455, 465, 589, 676
See application file for complete search history.

(56) References Cited

U.S. PATENT DOCUMENTS

| | | | | |
|---|---|---|---|---|
| 4,314,810 A | * | 2/1982 | Fourcadier et al. ............. | 8/410 |
| 2003/0066141 A1 | | 4/2003 | Oshika et al. | |

FOREIGN PATENT DOCUMENTS

| | | |
|---|---|---|
| JP | 2001 294520 | 10/2001 |
| JP | 2002 241246 | 8/2002 |
| JP | 2005 170838 | 6/2005 |
| JP | 2005 179210 | 7/2005 |
| JP | 2006 160641 | 6/2006 |
| JP | 2006 315978 | 11/2006 |
| JP | 2007 63199 | 3/2007 |
| JP | 2007 126384 | 5/2007 |

OTHER PUBLICATIONS

STIC Search Report dated Sep. 24, 2010.*
U.S. Appl. No. 12/682,071, filed Apr. 8, 2010, Fukuhara, et al.

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

A non-oxidative hair dye composition containing the components (a) and (b): (a) one or two or more kinds of a glycylglycine derivative represented by the following formula (1) and having two or three amino acid residues or salts thereof, and wherein Y represents an amino acid residue or a bivalent group represented by the formula (2); and (b) a direct dye;

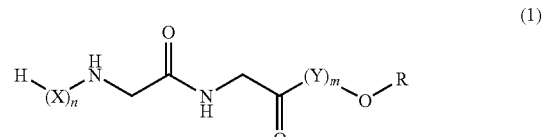

(1)

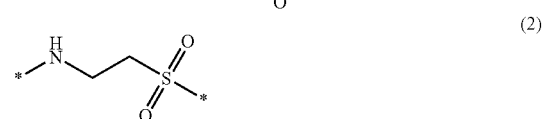

(2)

Wherein symbol * and R, X, n and m are defined in the claims and in the disclosure.

5 Claims, No Drawings

NON-OXIDATIVE HAIR DYE COMPOSITION

FIELD OF THE INVENTION

The present invention relates to a non-oxidative hair dye composition and a method for dyeing hair using the same.

BACKGROUND OF THE INVENTION

Hair dye compositions can be classified according to the presence or absence of a bleaching action against the dye used or melanin. Representative examples of the hair dye compositions include a two-component oxidative hair dye composition which includes a first part containing an alkali agent, an oxidation dye, and optionally a direct dye such as a nitro dye, and a second part containing an oxidizing agent; and a one-component non-oxidative hair dye composition containing a pH adjusting agent (an acid or an alkali), and at least one direct dye such as an acid dye, a basic dye, and a nitro dye.

The one-component non-oxidative hair dye composition does not contain an oxidizing agent such as hydrogen peroxide, and therefore is advantageous in that the hair dye composition causes less chemical damages to the hair and can be used for hair with a background of various chemical treatments such as hair dyeing treatment or permanent treatment. However, the one-component non-oxidative hair dye composition also has a defect of being poor in shampoo fastness (color durability) as compared with the two-component hair dye composition.

Thus, in order to increase dyeing properties, there have been suggested a technology of accelerating the penetration of a direct dye into the hair using various organic solvents (Patent Document 1), a hair dye pretreatment agent containing L-theanine and a water-soluble polymer (Patent Document 2), or an acidic hair dye pretreatment agent containing urea and benzyl alcohol (Patent Document 3).

The above-mentioned technologies can enhance dyeing properties and at the same time, enhance shampoo fastness. However, enhancing dyeing properties occasionally results in undesirable effects in which the color tone repeatedly changes. Thus, it was essential for their technologies to readjust the color tone.

Meanwhile, as a technology for enhancing shampoo fastness, there has been suggested a post-treatment agent for dyed hair containing a hydroxyalkanesulfonic acid having 2 to 5 carbon atoms, or a salt thereof (Patent Document 4). However, since a combined use with this post-treatment agent makes the treatment more complicated, the method cannot be said to be necessarily a convenient method for dyeing hair, and this method has room for improvement.

Patent Document 1: JP-A-2002-241246
Patent Document 2: JP-A-2007-63199
Patent Document 3: JP-A-2007-126384
Patent Document 4: JP-A-2001-294520

SUMMARY OF THE INVENTION

The present invention provides a non-oxidative hair dye composition containing the following components (a) and (b):

(a) one or two or more kinds of a glycylglycine derivative represented by the following formula (1) and having two or three amino acid residues, or salts thereof; and (b) a direct dye.

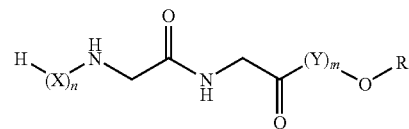

[wherein X represents a bivalent hydrocarbon group having 1 to 4 carbon atoms which may be substituted with a hydroxyl group, or an amino acid residue;

Y represents an amino acid residue, or a bivalent group represented by the following formula (2):

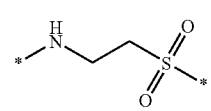

(wherein symbol -* represents a bond that binds to an adjacent carbonyl group or oxygen atom);

R represents a hydrogen atom, or a monovalent hydrocarbon group having 1 to 4 carbon atoms in which the hydroxyl group may be substituted; and m and n each represent 0 or 1, provided that when both m and n represent 1, X cannot be an amino acid residue].

The present invention also provides a method for dyeing hair, including applying the non-oxidative hair dye composition to the hair, subsequently leaving the hair dye composition on the hair for 1 to 60 minutes, and rinsing the hair dye composition.

DETAILED DESCRIPTION OF THE INVENTION

The present invention provides a non-oxidative hair dye composition having excellent shampoo fastness. The present invention also provides a method for dyeing hair with excellent shampoo fastness.

The inventors of the present invention paid attention to various utilizable proteins, and among them, particularly to marine proteins derived from fish scale or fish skin, which are attracting more attention in recent years, and examined the dyeing properties of a non-oxidative hair dye composition containing hydrolysates of those proteins. As a result, the inventors obtained a finding that the shampoo fastness is enhanced. Furthermore, the inventors conducted more detailed investigations, and obtained a finding that it is not necessarily required to use protein hydrolysates, and specific oligopeptides may be used. That is, the inventors found that a non-oxidative hair dye composition containing a glycylglycine derivative having a specific structure and a direct dye, imparts excellent shampoo fastness.

When the non-oxidative hair dye composition of the present invention is used, high shampoo fastness can be manifested, without largely changing the color tone, and high shampoo fastness is realized even if widely-used conventional dyes are used. Furthermore, according to the present invention, there is provided a method for dyeing hair, which makes it possible to manifest high shampoo fastness.

Hair dyes are roughly classified into oxidative hair dyes and non-oxidative hair dyes. According to the present invention, a hair dye which makes use of an independent composition containing an oxidizing agent as a constituent element is designated as an oxidative hair dye, and a hair dye which does not make use of an independent composition containing an oxidizing agent as a constituent element is designated as a non-oxidative hair dye. Accordingly, for example, an air-oxidative hair dye, which does not make use of an independent composition containing an oxidizing agent as a constituent element, is a non-oxidative hair dye according to the present invention.

The form of the non-oxidative hair dye of the present invention is intended to include a one-component hair dye containing the components (a) and (b) in a single preparation, as well as a form obtained by combining a conventional (known or commercially available) one-component hair dye with an independent composition containing the component (a). Furthermore, the term "whole composition" as used in the present invention refers to the entire composition used in a hair dyeing treatment, and in the case of the form obtained by combining a conventional one-component hair dye with an independent composition containing the component (a), the "whole composition" means a mixture obtained by mixing the one-component hair dye and the independent composition.

The component (a) is a mixture of one or two or more kinds of a glycylglycine derivative represented by the general formula (1) or salts thereof, and may be in a free form or may be in the form of amphoteric ion.

Examples of the salts of the glycylglycine derivative include inorganic acid salts such as hydrochloride and sulfate; organic acid salts such as lactate; ammonium salts such as ammonium salts and alkylammonium salts; alkali metal salts such as sodium salts.

In the general formula (1), the bivalent hydrocarbon group having 1 to 4 carbon atoms which may be substituted with a hydroxyl group, as represented by X, may be saturated or unsaturated, and may be a linear or branched chain. Among these, a bivalent saturated hydrocarbon group substituted with a hydroxyl group, or a bivalent saturated hydrocarbon group is preferred.

Examples of the bivalent hydrocarbon group include a methylene group, an ethylene group, an ethylidene group, a vinylene group, a trimethylene group, an isopropylidene group, a 1-propenylene group, a tetramethylene group, a 2-methyltrimethylene group, a 1-methyltrimethylene group, a 1-butenylene group, and the like.

Examples of the bivalent hydrocarbon group substituted with a hydroxyl group include a 1-hydroxyethylene group, a 1-hydroxytrimethylene group, a 1,2-dihydroxytrimethylene group, a 1-hydroxytetramethylene group, a 1,2-dihydroxytetramethylene group, a 1,3-dihydroxytetramethylene group, a 1,2,3-trihydroxytetramethylene group, and the like.

The term "amino acid residue" as used in the present invention means a unit amino acid moiety that is intended to form an oligopeptide, which is obtained by synthesis or is derived from all amino acids that are present in the living body. The "amino acid residue" may adopt a D-form or an L-form.

In the general formula (1), the amino acid residue represented by X may be an basic amino acid residue such as an arginine residue, a lysine residue or a histidine residue; an aliphatic amino acid residue such as an alanine residue or a glycine residue; an aromatic amino acid residue such as a phenylalanine residue, a tyrosine residue or a tryptophan residue; an acid amide amino acid residue such as a glutamic residue or an aspartic residue; an acidic amino acid residue such as a glutamic acid residue, an aspartic acid residue or a cysteic acid residue; a hydroxyamino acid residue such as a serine residue or a threonine residue; a cyclic amino acid residue such as a proline residue, an N-methylproline residue or a 4-hydroxyproline residue. Among them, an arginine residue, an alanine residue, a phenylalanine residue, a glycine residue, a glutamine residue, a glutamic acid residue, a serine residue, a proline residue, an N-methylproline residue, and a 4-hydroxyproline residue are preferred.

In the general formula (1), the monovalent hydrocarbon group having 1 to 4 carbon atoms which may be substituted with a hydroxyl group, as represented by R, may be saturated or unsaturated, and may be a linear or branched chain.

The monovalent hydrocarbon group is preferably an alkyl group, and examples include a methyl group, an ethyl group, a propyl group, a butyl group, an isopropyl group, an isobutyl group, an s-butyl group, a t-butyl group, and the like.

The monovalent hydrocarbon group substituted with a hydroxyl group is preferably a hydroxyalkyl group, and examples include a hydroxymethyl group, a 2-hydroxyethyl group, a 3-hydroxypropyl group, a 4-hydroxybutyl group, a 2,3-dihydroxyethyl group, a 2,3,4-trihydroxybutyl group, a 2,4-dihydroxybutyl group, and the like.

In the general formula (1), the amino acid residue represented by Y may be, for example, the same amino acid residues as those represented by X, Y is preferably an arginine residue, an alanine residue, a glycine residue, a glutamine residue, a glutamic acid residue, a serine residue, a proline residue, a 4-hydroxyproline residue, or a bivalent group represented by general formula (2):

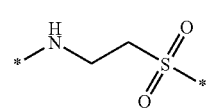

(2)

(wherein symbol -* represents a bond that binds to an adjacent carbonyl group or oxygen atom).

Examples of glycylglycine derivatives that are suitable for the component (a) include the glycylglycine derivatives represented by general formulas (G1) to (G9), and general formulas (G2) to (G9) are more preferred, while general formulas (G8) and (G9) are even more preferred. These glycylglycine derivatives may be in their free forms, may be in the form of amphoteric ion, or may be in the form of salt. These may also be used alone, or in combination of two or more kinds.

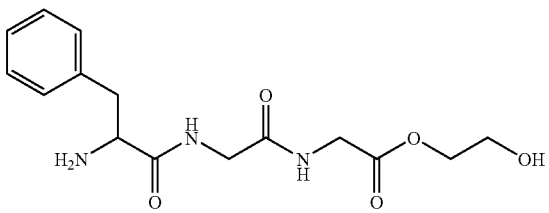

(G1)

-continued

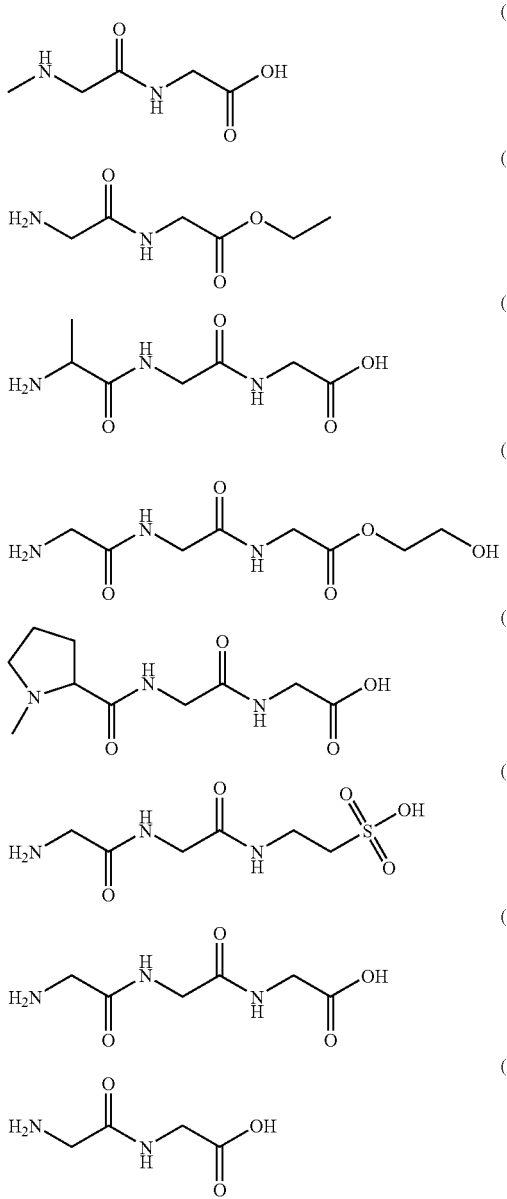

The content of the component (a) is preferably 0.05 to 10% by mass, and more preferably 0.25 to 5% by mass, based on the whole composition, from the viewpoint of suppressing change in a color tone and obtaining storage stability.

Examples of the direct dye include acid dyes, nitro dyes, disperse dyes, basic dyes, the direct dyes described in JP-A-2003-342139, and the like.

Examples of the acid dyes include Blue No. 1, Violet No. 401, Black No. 401, Orange No. 205, Red No. 227, Red No. 106, Yellow No. 203, Acidic Orange No. 3, and the like.

Examples of the nitro dyes include 2-nitro-para-phenylenediamine, 2-amino-6-chloro-4-nitrophenol, 3-nitro-p-hydroxyethylaminophenol, 4-nitro-ortho-phenylenediamine, 4-amino-3-nitrophenol, 4-hydroxypropylamino-3-nitrophenol, HC Blue No. 2, HC Orange No. 1, HC Red No. 1, HC Yellow No. 2, HC Yellow No. 4, HC Yellow No. 5, HC Red No. 3, N,N-bis(2-hydroxyethyl)-2-nitro-para-phenylenediamine, and the like.

Examples of the disperse dyes include Disperse Violet No. 1, Disperse Blue No. 1, Disperse Black No. 9, and the like.

Examples of the basic dyes include Basic Blue No. 99, Basic Brown No. 16, Basic Brown No. 17, Basic Red No. 76, Basic Red No. 51, Basic Yellow No. 57, Basic Yellow No. 87, Basic Orange No. 31, and the like.

The direct dye can be appropriately used alone or in combination of two or more kinds, in accordance with the pH of the system. When the pH of the system is 2 or more but less than 6 at 25° C., an acid dye and/or a nitro dye is preferable. When the pH of the system is 6 or more but less than 12 at 25° C., a nitro dye and/or a basic dye is preferable.

The content of the direct dye is preferably 0.001 to 5% by mass, and more preferably 0.01 to 3% by mass.

The non-oxidative hair dye of the present invention can contain the organic solvent as a component (c). Examples of the organic solvent include lower alkanols such as ethanol and 2-propanol; aromatic alcohols such as benzyl alcohol and benzyloxyethanol; polyols such as propylene glycol, 1,3-butanediol, diethylene glycol and glycerin; cellosolves such as ethylcellosolve and butylcellosolve; and carbitols such as ethylcarbitol and butylcarbitol.

As the pH adjusting agent that is used in the non-oxidative hair dye composition of the present invention, ammonia and salts thereof; alkanolamines such as monoethanolamine, isopropanolamine, 2-amino-2-methylpropanol and 2-aminobutanol, and salts thereof; alkanediamines such as 1,3-propanediamine, and salts thereof; carbonic acid salts such as guanidine carbonate, sodium carbonate, potassium carbonate, sodium hydrogen carbonate and potassium hydrogen carbonate; and the like can be used as alkali agents.

Furthermore, as acid agents, inorganic acids such as hydrochloric acid and phosphoric acid; organic acids such as citric acid, glycolic acid and lactic acid; hydrochloric acid salts such as hydrochloric acid monoethanolamine; phosphoric acid salts such as monopotassium dihydrogen phosphate and disodium monohydrogen phosphate; and the like can be used.

The pH adjusting agents are such that an acid agent alone or an alkali agent alone may be used, or the two agents may be used in combination. The content of the pH adjusting agent is preferably 0.05 to 15% by mass, more preferably 0.1 to 10% by mass, and even more preferably 0.2 to 5% by mass, based on the whole composition, from the viewpoint of obtaining sufficient dyeing effects, and from the viewpoint of reducing hair damages or scalp stimulation.

Further, the non-oxidative hair dye can contain any surfactant. As the surfactant, a cationic surfactant, a nonionic surfactant, an amphoteric surfactant and an anionic surfactant may all be used.

The cationic surfactant is preferably, for example, a mono-long-chain alkyl quaternary ammonium salt. Specific examples include cetrimonium chloride, steartrimonium chloride, behentrimonium chloride, stearalkonium chloride, benzalkonium chloride, and the like, and steartrimonium chloride and behentrimonium chloride are more preferred.

Examples of the nonionic surfactant include polyoxyalkylene alkyl ether, polyoxyalkylene alkenyl ether, higher fatty acid sucrose ester, polyglycerin fatty acid ester, higher fatty acid mono- or diethanolamide, polyoxyethylene hydrogenated castor oil, polyoxyethylene sorbitan fatty acid ester, polyoxyethylene sorbite fatty acid ester, alkylsaccharide, alkylamine oxide, alkylamidoamine oxide, and the like. Among these, polyoxyalkylene alkyl ether and polyoxyethylene hydrogenated castor oil are preferred, and polyoxyethylene alkyl (C12-14) ether is more preferred.

Examples of the amphoteric surfactant include imidazoline, carbobetaine, amidobetaine, sulfobetaine, hydroxysulfobetaine, amidosulfobetaine, and the like.

Examples of the anionic surfactant include alkylbenzenesulfonate, alkyl or alkenyl ether sulfate, alkyl or alkenyl sulfate, olefin sulfonate, alkanesulfonate, saturated or unsaturated fatty acid salt, alkyl or alkenyl ether carboxylate, α-sulfone fatty acid salt, N-acylamino acid, phosphoric acid mono- or diester, sulfosuccinic acid ester, and the like. Examples of alkyl ether sulfate include polyoxyethylene alkyl ether sulfate. Examples of the counterion of the anionic group of these anionic surfactants include alkali metal ions such as sodium ion and potassium ion; alkaline earth metal ions such as calcium ion and magnesium ion; ammonium ion; and alkanolamine having one to three alkanol groups, each having 2 or 3 carbon atoms (for example, monoethanolamine, diethanolamine, triethanolamine, triisopropanolamine, and the like).

The content of the surfactant is preferably 0.1 to 10% by mass, and more preferably 0.5 to 8% by mass, based on the total mass of the composition, from the viewpoint of the feel to the touch and the emulsifying performance.

The non-oxidative hair dye composition of the present invention may contain a cationic polymer for the purpose of enhancing the feel of touch when used or after hair dyeing.

The cationic polymer refers to a polymer having a cationic group or a group that can be ionized into a cationic group, and also includes amphoteric polymers which are cationic on the whole. That is, the cationic polymer may be a water-soluble polymer containing an amino group or an ammonium group in a side chain of the polymer chain, or a water-soluble polymer containing a diallyl quaternary ammonium salt as a constituent unit. Specific examples include cationized celluloses, cationic starch, cationized guar gum, polymers or copolymers of a diallyl quaternary ammonium salt, quaternized polyvinylpyrrolidone, and the like. Among these, polymers containing a diallyl quaternary ammonium salt as a constituent unit, quaternized polyvinylpyrrolidone and cationized cellulose are preferred from the viewpoint of the effects on softness, smoothness and easy finger-combing during shampooing, and easy manageability and moisture retention during drying, and stability of the agent, and polymers or copolymers of a diallyl quaternary ammonium salt, and cationized cellulose are more preferred.

Specific examples of the cationic polymer include dimethyldiallylammonium chloride polymers (polyquaternium-6, for example, Merquat 100; Nalco Company), dimethyldiallylammonium chloride/acrylic acid copolymers (polyquaternium-22, for example, Merquat 280 and 295; Nalco Company), dimethyldiallylammonium chloride/acrylamide copolymers (polyquaternium-7, for example, Merquat 550; Nalco Company), quaternized polyvinylpyrrolidone (Gafquat 734, Gafquat 755 and Gafquat 755N; ISP Japan, Ltd.), cationized cellulose (Reogard G and Reogard GP; Lion Cop., Polymer JR-125, Polymer JR-400, Polymer JR-30M, Polymer LR-400, and Polymer LR-30M; Union Carbide Corp.), and the like.

These cationic polymers may be used alone, or in combination or two or more kinds. The content of the cationic polymer is preferably 0.001 to 10% by mass, more preferably 0.01 to 8% by mass, and even more preferably 0.05 to 5% by mass, based on the total mass of the composition, from the viewpoints of a touch-feeling enhancing effect and prescription stability.

The non-oxidative hair dye composition of the present invention may be incorporated with a water-soluble polymer for the purpose of preventing drips upon use and preventing the attachment of dirt to the scalp or the like. Examples of the water-soluble polymer include gum arabic, carrageenan, karaya gum, tragacanth gum, carob gum, quince seed (*Cydonia oblonga*), casein, dextrin, gelatin, sodium pectinate, sodium alginate, methylcellulose, ethylcellulose, carboxymethylcellulose (CMC), hydroxyethylcellulose, hydroxypropylcellulose, polyvinyl alcohol (PVA), polyvinyl methyl ether (PVM), polyvinylpyrrolidone (PVP), polyacrylic acid sodium, locust bean gum, guar gum, tamarind gum, dialkyldimethylammonium sulfate cellulose, xanthan gum, modified xanthan gum, aluminum magnesium silicate, bentonite, and the like. Among these, hydroxyethylcellulose, xanthan gum, and modified xanthan gum are preferred. One or more of these water-soluble polymers may be used, and it is preferable to incorporate the water-soluble polymer at a proportion of 0.1 to 10% by mass, and more preferably 0.5 to 5% by mass, based on the whole composition.

It is preferable that the non-oxidative hair dye composition of the present invention contains silicone so as to impart an excellent feeling upon use.

Examples of the silicone include polysiloxanes, modified silicones (for example, amino-modified silicones, fluorine-modified silicones, alcohol-modified silicones, polyether-modified silicones, epoxy-modified silicones, alkyl-modified silicones, and the like), and cyclic polysiloxanes, and polysiloxanes and amino-modified silicones are preferred.

These silicones are commercially available, and for example, BY11-026, BY22-19, FZ-3125, SH200-1,000,000 cs (Dow Corning Toray Co., Ltd.), TSF451-100MA (Momentive Performance Materials Japan LLC) [all being polysiloxanes]; TSF4440 (Momentive Performance Materials Japan LLC), KF-6005, KF-6011 (Shin-Etsu Chemical Co., Ltd.) [all being polyether-modified silicones]; SF8451C, SF8452C, SF8457C, SM8704C, SM8904 (Toray Dow Corning Silicone Co., Ltd.), KF-867 (Shin-Etsu Chemical Co., Ltd.) [all being amino-modified silicones]; and the like may be mentioned.

The content of the silicone is preferably 0.02 to 20% by mass, more preferably 0.1 to 10% by mass, and even more preferably 0.2 to 5% by mass, based on the total mass of the composition, from the viewpoint of obtaining sufficient effects and suppressing stickiness.

It is preferable that the non-oxidative hair dye composition of the present invention contains a higher alcohol from the viewpoint of improving the feel to the touch and obtaining stability. The higher alcohol can form a structure with the surfactant, to thereby prevent separation of the hair dye composition as well as to improve the feel to the touch during rinsing.

The higher alcohol is preferably an alcohol having 8 to 22 carbon atoms, and more preferably 16 to 22 carbon atoms. Specific examples include cetanol, stearyl alcohol, behenyl alcohol, and the like, and mixtures of these may also be used.

The higher alcohols may be used alone or in combination of two or more kinds. The content thereof is preferably 0.01 to 15% by mass, and more preferably 0.1 to 10% by mass, based on the total mass of the composition.

The formulation of the non-oxidative hair dye composition of the present invention may be in the form of, for example, solution, emulsion, cream, gel, paste, mousse, aerosol, or the like.

It is desirable for the non-oxidative hair dye composition of the present invention to have a viscosity enough to prevent dripping when the respective components constituting the hair dye composition are mixed and applied to the hair, and for example, the viscosity of the whole composition measured at 25° C. using a type B rotary viscometer equipped with a helical stand (B8R type viscometer, TOKIMEC, Inc.) is preferably 2000 to 100,000 mPa·s. Here, the viscosity is a value obtained after rotating the composition for one minute at 10 rpm using a Rotor T-C.

The non-oxidative hair dye composition of the present invention may be used by applying in an amount 0.1-fold to 10-fold the mass of the hair. In the case of a form obtained by combining a known or commercially available one-component hair dye containing the component (b) with a composition containing the component (a), these may be applied by mixing in a mixing vessel or by mixing on the hair of the scalp. As the method of treatment, for example, a method of applying the hair dye composition to the hair, subsequently leaving the hair dye composition for a predetermined time, rinsing the hair dye composition, and drying, is employed. The temperature for the application to the hair is preferably 15 to 45° C., and the time of application is preferably 1 to 60 minutes. In this case, the hair dye composition may be lightly rinsed with water, and subsequently the hair may be washed using a shampoo containing an anionic surfactant and then rinsed with water. When the hair dye composition contains a cationic polymer and a silicone, after the cationic polymer appropriately being washed out, the silicone appropriately remains behind on the hair. Thus, satisfactory regulatory effects can be imparted. The shampoo may be suitably a general aqueous shampoo containing about 5 to 20% by mass of an anionic surfactant such as sodium lauryl sulfate, sodium laureth-1 sulfate, sodium laureth-2 sulfate or sodium laureth-3 sulfate.

EXAMPLES

Examples 1 to 3 and Comparative Example 1

Non-oxidative hair dye compositions formed from the compositions shown in Table 1 were prepared by conventional methods. The obtained hair dye compositions were subjected to an evaluation of dyeing properties and shampoo fastness according to the following methods.

[Dyeing Properties]

Chinese white hair was treated with a commercially available permanent treating agent, and thus 1 g of a tress of perm-damaged hair was prepared. A hair dye composition was applied to the perm-damaged hair at a bath ratio (hair dye:hair=1:1), and the hair tress was left to stand for 15 minutes at 30° C., and then was rinsed with water at about 40° C. The hair tress was cleansed with a commercially available shampoo, washed with water, applied with a commercially available hair rinse, and then rinsed with water. The hair tress was wiped with a towel and dried with a hair dryer. The color tone of the hair tress obtained immediately after hair dyeing was measured with the CIE color coordinate system (L*, a*, b*) using a colorimeter (Chroma meter CR-400 manufactured by Konica Minolta Sensing, Inc.), and the difference between the color tones obtained before dyeing and after dyeing was determined by the following formula and was designated as dyeing properties $\Delta E^*_0$. A larger value of $\Delta E^*$ indicates more excellent dyeing properties.

$$\Delta E_0^* = \sqrt{(L_1^* - L_0^*)^2 + (a_1^* - a_0^*)^2 + (b_1^* - b_0^*)^2} \quad \text{[Mathematical formula 1]}$$

wherein $L^*_0$, $a^*_0$ and $b^*_0$ respectively represent the values of L*, a* and b* before dyeing, and $L^*_1$, $a^*_1$ and $b^*_1$ respectively represent the values of L*, a* and b* immediately after dyeing.

[Shampoo Fastness]

Subsequently, a process of immersing the hair tress in a solution prepared by diluting a commercially available shampoo to a concentration of 10% and maintaining at 40° C., for one minute at 40° C., and then drying the hair tress for 15 minutes with a hair dryer, was repeated five times. Subsequently, the color tone of the hair tress was measured again using a color coordinate system.

The color tint $\Delta E^*_S$ of the thus-obtained hair tress after repeated shampoo cleansing was determined by the following formula, and the difference between $\Delta E^*_0$ and $\Delta E^*_S$ was determined to thereby calculate the shampoo fastness $\Delta\Delta E^*$. A smaller value of $\Delta\Delta E^*$ indicates more excellent shampoo fastness.

$$\Delta E_S^* = \sqrt{(L_2^* - L_0^*)^2 + (a_2^* - a_0^*)^2 + (b_2^* - b_0^*)^2} \quad \text{[Mathematical formula 2]}$$

wherein $L^*_0$, $a^*_0$ and $b^*_0$ respectively represent the values of L*, a* and b* before dyeing, and $L^*_2$, $a^*_2$ and $b^*_2$ respectively represent the values of L*, a* and b* after shampoo cleansing.

$$\Delta\Delta E^* = \Delta E^*_0 - \Delta E^*_S$$

The dyeing properties and shampoo fastness were respectively determined for two tresses of hair, and the average values are presented together in Table 1.

TABLE 1

| Component (mass %) | Example 1 | Example 2 | Example 3 | Comparative Example 1 |
|---|---|---|---|---|
| Glycylglycine (G9) | 0.50 | 2.00 | — | — |
| Glycylglycylglycine (G8) | — | — | 2.00 | — |
| Orange No. 205 | 0.48 | 0.48 | 0.48 | 0.48 |
| Black No. 401 | 0.28 | 0.28 | 0.28 | 0.28 |
| Violet No. 401 | 0.03 | 0.03 | 0.03 | 0.03 |
| Red No. 227 | 0.04 | 0.04 | 0.04 | 0.04 |
| Aqueous solution of glycolic acid (71 mass %) | 4.00 | 4.00 | 4.00 | 4.00 |
| Ethanol | 10.00 | 10.00 | 10.00 | 10.00 |
| Benzyloxyethanol | 10.00 | 10.00 | 10.00 | 10.00 |
| Glycerin | 2.00 | 2.00 | 2.00 | 2.00 |
| (C12-14) Pareth-9 | 0.24 | 0.24 | 0.24 | 0.24 |
| PEG-9 dimethicone*[1] | 0.80 | 0.80 | 0.80 | 0.80 |
| PEG-11 methyl ether dimethicone*[2] | 0.80 | 0.80 | 0.80 | 0.80 |
| Hydroxypropylxanthan gum*[3] | 1.40 | 1.40 | 1.40 | 1.40 |
| 48 mass % aqueous solution of sodium hydroxide | q.s.*[4] | q.s.*[4] | q.s.*[4] | q.s.*[4] |
| Fragrance | 0.16 | 0.16 | 0.16 | 0.16 |
| Purified water | Balance | Balance | Balance | Balance |
| Total | 100.0 | 100.0 | 100.0 | 100.0 |
| Dyeing properties ($\Delta E^*_0$) | 56.5 | 56.6 | 56.6 | 56.5 |
| Shampoo fastness ($\Delta\Delta E^*$) | 0.69 | 0.85 | 0.66 | 1.38 |

*[1]KF-6005, Shin-Etsu Chemical Co., Ltd.
*[2]KF-6011, Shin-Etsu Chemical Co., Ltd.
*[3]Rhaball Gum EX, Dainippon Sumitomo Pharma Co., Ltd.
*[4]Amount to adjust the pH to 3

As shown in Table 1, the non-oxidative hair dye compositions of Examples 1 to 3 were excellent in shampoo fastness as compared with the Comparative Example 1.

Examples 4 to 6

The non-oxidative hair dye compositions shown in Table 2 (Examples 4 to 6) are prepared. When each of these hair dye compositions is applied in an equal amount to 1 g of a tress of human hair that is mixed with white hair at a ratio of 10%, and the hair tress is left to stand for 30 minutes, washed with water, cleansed with a shampoo and dried, dyed hair having good shampoo fastness may be obtained.

TABLE 2

| Component (mass %) | Example 4 | Example 5 | Example 6 |
| --- | --- | --- | --- |
| Glycylglycine (G9) | 1.00 | — | 0.10 |
| Methyl glycylglycine (G2) | — | 0.35 | 0.25 |
| Glycylglycine ethyl (G3) | — | 0.25 | 0.10 |
| HC Red No. 3 | 0.20 | 0.30 | 0.30 |
| HC Yellow No. 4 | 0.20 | — | — |
| Basic Yellow No. 57 | — | 0.20 | 0.10 |
| Basic Blue No. 99 | 0.30 | 0.20 | 0.10 |
| Aqueous ammonia (28 mass %) | 8.00 | 8.00 | 8.00 |
| Isopropanol | 1.50 | 1.50 | 1.50 |
| Ethanol | 6.00 | 6.00 | 5.00 |
| Benzyl alcohol | 8.00 | 8.00 | 8.00 |
| PEG-12 | — | — | 0.50 |
| Ammonium chloride | q.s.*[7] | q.s.*[7] | q.s.*[7] |
| Hydroxypropylxanthan gum*[5] | 2.00 | 2.00 | 2.00 |
| PEG-9 dimethicone*[6] | — | 1.50 | 1.50 |
| Purified water | Balance | Balance | Balance |
| Total | 100.0 | 100.0 | 100.0 |

*[5]Rhaball Gum EX, Dainippon Sumitomo Pharma Co., Ltd.
*[6]KF-6005, Shin-Etsu Chemical Co., Ltd.
*[7]Amount to adjust the pH to 10

Example 7

The one-component hair dye of foam type shown in Table 3 is prepared. When an equal amount of the hair dye composition is applied to 1 g of a tress of black hair that has been bleached with a commercially available bleaching agent, and the hair tress is left to stand for 30 minutes, washed with water, cleansed with a shampoo and dried, dyed hair having good shampoo fastness may be obtained.

TABLE 3

| Component (mass %) | Example 7 |
| --- | --- |
| Alanylglycylglycine (G4) | 0.50 |
| Basic Brown No. 16 | 0.30 |
| HC Yellow No. 2 | 0.20 |
| HC Yellow No. 4 | 0.30 |
| Basic Red No. 76 | 0.60 |
| Basic Blue No. 99 | 0.10 |
| Aqueous ammonia (28 mass %) | 8.00 |
| Isopropyl alcohol | 3.50 |
| Laureth-23 | 0.50 |
| Benzyl alcohol | 8.00 |
| Oleic acid | 7.50 |
| LPG (4.0 kg/cm$^2$) | 10.00 |
| Ammonium chloride | q.s.*[8] |
| Purified water | Balance |
| Total | 100.0 |

*[8]Amount to adjust the pH to 10

Example 8

A non-oxidative hair dye shown in Table 4 (Agent A) and a non-oxidative hair dye shown in Table 5 (Agent B) are respectively prepared. When 100 g of the non-oxidative hair dye, Agent A, is mixed with 10 g of the non-oxidative hair dye, Agent B, the mixture is applied to the hair of the scalp, and the hair is left to stand for 20 minutes, washed with water, cleansed with a shampoo and dried, dyeing with satisfactory shampoo fastness is achieved.

TABLE 4

| Component (mass %) | Non-oxidative hair hair dye, Agent A |
| --- | --- |
| Direct dye (E1) | 0.1 |
| Direct dye (E2) | 0.2 |
| HC Red No. 3 | 0.3 |
| Basic Yellow No. 57 | 0.1 |
| Basic Blue No. 99 | 0.1 |
| Ammonia (28 mass %) | 8.0 |
| Isopropyl alcohol | 1.5 |
| Ethanol | 5.0 |
| Benzyl alcohol | 8.0 |
| PEG-12 | 0.5 |
| Ammonium chloride*[9] | q.s. |
| Hydroxypropylxanthan gum | 2.0 |
| PEG-9 dimethicone*[10] | 1.5 |
| Purified water | Balance |
| Total | 100.0 |

*[9]Amount to adjust the pH to 10
*[10]KF-6005, Shin-Etsu Chemical Co., Ltd.

Direct dye (E1)

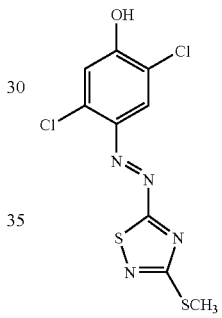

Direct dye (E2)

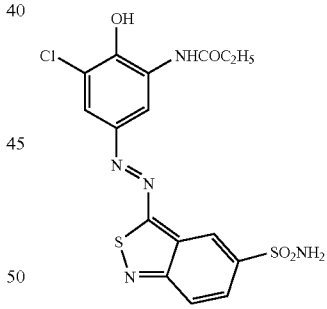

TABLE 5

| Component (mass %) | Non-oxidative hair dye, Agent B |
| --- | --- |
| Glycylglycine (G9) | 10.0 |
| Ethanol | 10.0 |
| Benzyloxyethanol | 10.0 |
| Glycerin | 2.0 |
| PEG-9 dimethicone*[11] | 1.5 |
| Hydroxyethylcellulose*[12] | 0.5 |
| Purified water | Balance |
| Total | 100.0 |

*[11]KF-6005, Shin-Etsu Chemical Co., Ltd.
*[12]SE900, Daicel Chemical Industries, Ltd.

The invention claimed is:

1. A non-oxidative hair dye composition comprising the following components (a) and (b):

(a) one or two or more kinds of a glycylglycine derivative represented by the following formula (1) and having two or three amino acid residues, or salts thereof:

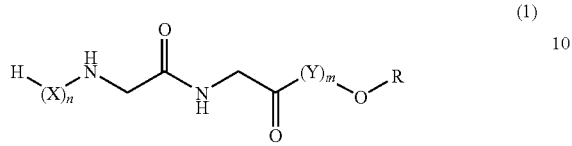
(1)

wherein X represents a bivalent hydrocarbon group having 1 to 4 carbon atoms which may be substituted with a hydroxyl group, or an amino acid residue;

Y represents an amino acid residue, or a bivalent group represented by the following formula (2):

(2)

wherein symbol -* represents a bond that binds to an adjacent carbonyl group or oxygen atom;

R represents a hydrogen atom, or a monovalent hydrocarbon group having 1 to 4 carbon atoms which may be substituted with a hydroxyl group; and m and n each represent 0 or 1, provided that when both m and n represent 1, X cannot be an amino acid residue; and (b) a direct dye.

2. The non-oxidative hair dye composition according to claim 1, wherein in the formula (1), X represents any one of an arginine residue, an alanine residue, a phenylalanine residue, a glycine residue, a glutamine residue, a glutamic acid residue, a serine residue, a proline residue, an N-methylproline residue, a 4-hydroxyproline residue and a saturated bivalent hydrocarbon group having 1 to 4 carbon atoms;

Y represents any one of an arginine residue, an alanine residue, a glycine residue, a glutamine residue, a glutamic acid residue, a serine residue, a proline residue, a 4-hydroxyproline residue, and a bivalent group represented by the formula (2); or R represents a hydrogen atom, or an alkyl group which may be substituted with a hydroxyl group.

3. The non-oxidative hair dye composition according to claim 1 or 2, wherein the glycylglycine derivative of the component (a) is glycylglycine or glycylglycylglycine.

4. The non-oxidative hair dye composition according to claim 1, further contains an organic solvent as a component (c).

5. A method for dyeing hair comprising applying the non-oxidative hair dye composition according to claim 1 to the hair, subsequently leaving the hair dye composition to stand for 1 to 60 minutes, and rinsing the hair dye composition.

* * * * *